United States Patent [19]

McCormack et al.

[11] Patent Number: 6,099,137
[45] Date of Patent: Aug. 8, 2000

[54] VEHICLE AIR FRESHENER POWERED FROM CIGARETTE LIGHTER RECEPTACLE

[76] Inventors: Larry G. McCormack, 1550 Owl Ridge, Colorado Springs, Colo. 80919; Garry R. Franklin, 11596 Wildflower Ct., Fishers, Ind. 46038; Terryl L. Oster, 5519 Brookmead Dr., Whittier, Calif. 90601

[21] Appl. No.: 09/198,662

[22] Filed: Nov. 23, 1998

[51] Int. Cl.[7] .................................................. F21V 33/00
[52] U.S. Cl. ............................ 362/96; 362/488; 392/390; 392/393; 219/202
[58] Field of Search ............................ 362/96, 542, 488; 422/125; 392/390, 393, 394, 395, 386; 219/267, 202

[56] References Cited

U.S. PATENT DOCUMENTS

| | | | |
|---|---|---|---|
| D. 306,644 | 3/1990 | Luthy | D23/366 |
| 2,898,649 | 8/1959 | Murray | 219/274 |
| 3,763,347 | 10/1973 | Whitaker | 219/271 |
| 4,346,059 | 8/1982 | Spector | 422/125 |
| 4,695,434 | 9/1987 | Spector | 422/116 |
| 4,714,984 | 12/1987 | Spector | 362/101 |
| 4,731,521 | 3/1988 | Spector et al. | 219/274 |
| 4,837,421 | 6/1989 | Luthy | 219/272 |
| 5,710,406 | 1/1998 | Garris et al. | 219/267 |
| 5,738,700 | 4/1998 | King | 362/96 |

*Primary Examiner*—Thomas M. Sember
*Attorney, Agent, or Firm*—William E. Hein

[57] ABSTRACT

An improved air freshener for use inside motor vehicles in which heat produced by a light bulb within the air freshener housing controls the release of fragrance from a removable fragrance impregnated pad positioned in close proximity to the light bulb. Light produced by the light bulb illuminates a translucent decorative cover mounted at the front of the air freshener.

1 Claim, 1 Drawing Sheet

VEHICLE AIR FRESHENER POWERED FROM CIGARETTE LIGHTER RECEPTACLE

BACKGROUND AND SUMMARY OF THE INVENTION

This invention relates generally to air fresheners and, more particularly, to an air freshener that is powered from a vehicle cigarette lighter receptacle. Automobile interiors tend, over time, to absorb smoke, pet, dirt, and grease odors, for example. These offensive odors generally cannot be removed by traditional shampooing or cleaning without major replacement of carpets and upholstery.

Prior art air fresheners have employed a variety of fragrances in attempts to mask the odors of automobile interiors. Some of these prior art devices hang from an interior auto fixture such as a mirror, and some are affixed to the inner surface of a window by means of a suction cup. These types of auto air fresheners are disadvantageous in that their fragrance is dissipated by simple evaporation and is generally contained in the immediate area of the device. Since these products do not deliver a fragrance throughout the interior of the automobile in which they are used, they are generally ineffective. Some types of prior art auto air fresheners are clipped or otherwise attached to air vents, resulting in the fragrance being distributed by the flow of cool or warm air from the automobile heating and air conditioning system. These devices are largely ineffective unless air is being blown across them. Since they typically employ a fragrance that dissipates more effectively with the application of hot air, they are much less effective during the months in which the vehicle air conditioning system is in primary use. The fragrance employed in these devices evaporates quite rapidly, so that they require replacement in a matter of days. Liquid air fresheners are either sprayed or poured on the carpets and other fabrics of automobile interiors, and the fragrance is left to dissipate on its own. Like hanging air fresheners, the fragrance is limited to the immediate area and the evaporative delivery cannot be controlled. These liquid and spray products tend to permanently stain and spot fabrics such as seats and carpets. They also tend to mix with the odors sought to be removed, thereby often exacerbating the offensive odor problem. When using these liquid air fresheners, the consumer changes the fragrance of choice regularly. Mixing fragrances often produces an unappealing and, sometimes, overwhelming result.

Exemplary of prior art air fresheners are those described in U.S. Pat. Nos. 4,714,984, 4,837,421, 4,695,434, and 4,346,059.

It would be advantageous to provide an improved air freshener for use inside motor vehicles in which the fragrance is slowly and controllably delivered to the interior of the vehicle. Such a device, adapted for insertion into the vehicle cigarette lighter receptacle, is provided in accordance with the illustrated preferred embodiment of the present invention. The present vehicle air freshener includes a light bulb, heat from which controls the amount of fragrance released from an internal fragrance cartridge, which may be easily changed at the end of its life or in the event a different fragrance is desired. Since usage can be controlled by simply plugging the present air freshener into or unplugging it from the cigarette lighter receptacle, it lasts longer than currently available air freshener products whose usage cannot be controlled, and it may be easily transferred from one vehicle to another.

DETAILED DESCRIPTION OF THE PREFERRED EMBODIMENT

Figure 1:
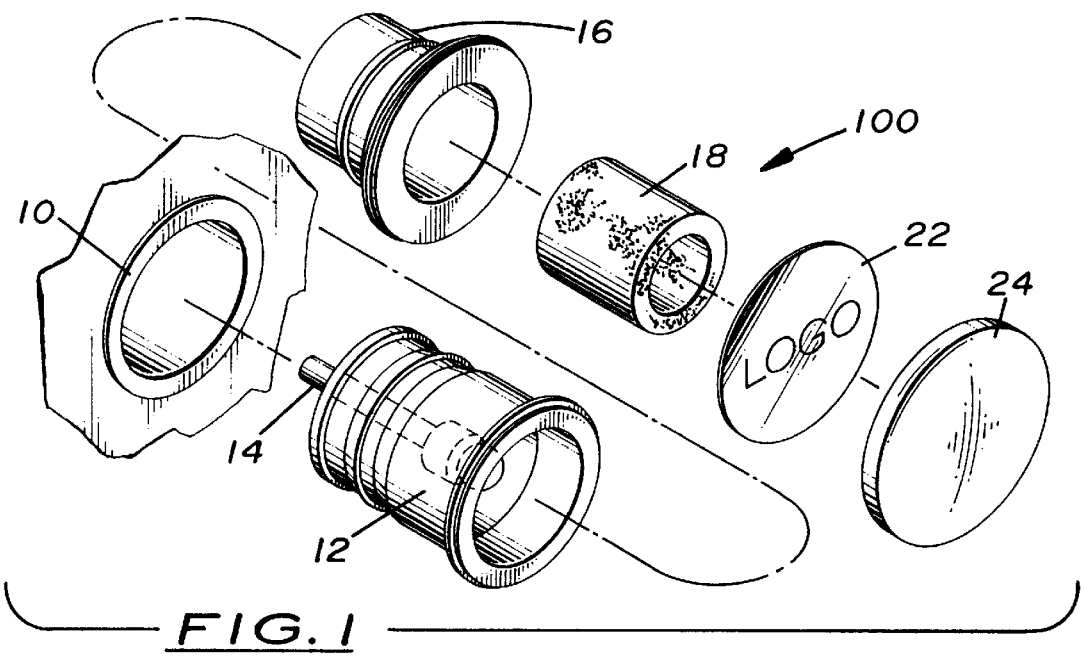
FIG. 1 is an exploded pictorial diagram illustrating a portion of a conventional vehicle cigarette lighter receptacle and the vehicle air freshener of the present invention.
Figure 2:
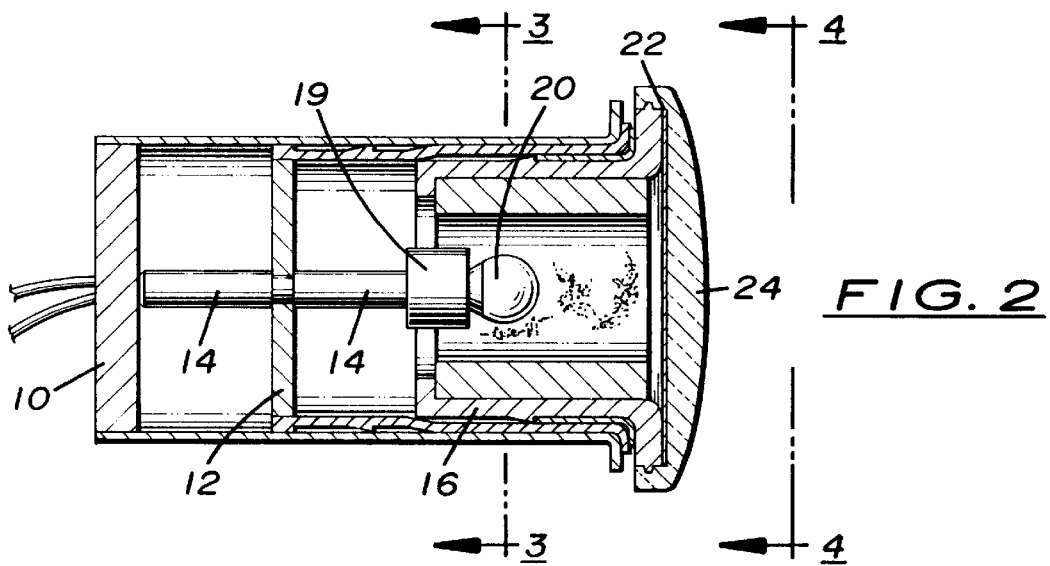
FIG. 2 is a longitudinal sectional diagram illustrating the vehicle air freshener of FIG. 1 in its assembled form inserted into a vehicle cigarette lighter receptacle.
Figure 3:
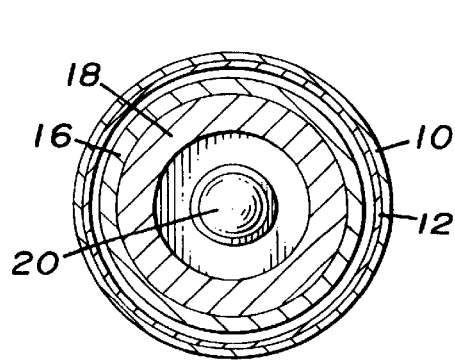
FIG. 3 is a sectional diagram taken along the line 3—3 of FIG. 2.
Figure 4:
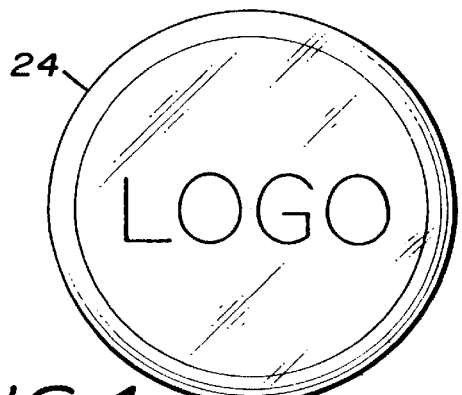
FIG. 4 is a sectional diagram taken along the line 4—4 of FIG. 2.

Referring now to FIGS. 1–4, there is shown a vehicle air freshener 100 in accordance with the present invention adapted for insertion into a conventional vehicle cigarette lighter receptacle 10. Vehicle air freshener 100 includes a first cylindrical housing member 12 having a rearwardly protruding electrode 14 adapted to make physical and electrical contact with a contact element centrally positioned on the rear wall of conventional vehicle cigarette lighter 10. A second cylindrical housing member 16 is adapted for removable retention within housing member 12. A bulb receptacle 19 is formed on a rear wall of housing member 16 to retain a conventional 12-volt light bulb 20. Electrode 14 is electrically connected to the base of light bulb 20 through bulb receptacle 19. A fragrance impregnated cylindrical pad 18 is provided to be removably inserted within housing member 16 such that light bulb 20 is cylindrically surrounded by fragrance impregnated pad 18. Fragrance impregnated pad 18 may comprise any one of a number of known materials such as felt or plastic, for example, that is capable of retaining a desired fragrance with which it is impregnated. A translucent disc 22 containing a desired decorative design or logo is held in place against a front surface of housing member 16 by a translucent cover 24 that removably snaps into position over housing member 16.

In use, the vehicle air freshener 100 is inserted into vehicle cigarette lighter 10, thereby providing electrical power to light bulb 20. Heat produced by light bulb 20 causes dissipation of the fragrance from fragrance impregnated pad 18. Light produced by light bulb 20 illuminates translucent disc 22 such that the decorative design or logo imprinted or otherwise provided thereon may be viewed through translucent cover 24. Operation of vehicle air freshener 100 may be turned off by simply unplugging it from cigarette lighter receptacle 10. The fragrance impregnated pad 18 may be conveniently changed, either because the fragrance has been exhausted through use or because a different fragrance is desired, by simply unsnapping cover 24 and removing disc 22 to permit access to pad 18.

We claim:

1. A vehicle air freshener powered from a vehicle cigarette lighter receptacle, comprising:

housing means adapted for insertion into the vehicle cigarette lighter receptacle, the housing means including a rearward protruding electrode for contacting a powered electrical contact within the cigarette lighter receptacle, said housing means comprising an outer cyclindical housing member and an inner cylindrical housing member adapted for removable retention within said outer cylindrical housing member, said inner cylindrical housing member including a bulb receptacle for retaining said light bulb;

a light bulb mounted within the housing means, the light bulb being electrically connected to the electrode;

fragrance retaining means positioned within the housing in close proximity to the light bulb to thereby receive heat generated by the light bulb, said fragrance retaining means comprising a cylindrical pad, impregnated with a desired fragrance, for insertion into said inner housing member so as to cylindrically surround said light bulb; and translucent cover means mounted at a forward end of the housing means for illumination by the light bulb, said translucent cover means comprising a translucent disc containing a desired decorative design and a translucent cover member adapted for being removably snapped into position over said translucent disc and said inner cylindrical housing member.

* * * * *